(12) United States Patent
Tokumoto et al.

(10) Patent No.: US 8,858,962 B2
(45) Date of Patent: Oct. 14, 2014

(54) ADJUVANT OR PHARMACEUTICAL PREPARATION FOR TRANSDERMAL OR TRANSMUCOSAL ADMINISTRATION

(75) Inventors: Seiji Tokumoto, Tsukuba (JP); Hirotoshi Adachi, Tsukuba (JP); Tetsuji Kuwahara, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 35 days.

(21) Appl. No.: 13/367,679

(22) Filed: Feb. 7, 2012

(65) Prior Publication Data

US 2012/0156258 A1    Jun. 21, 2012

Related U.S. Application Data

(63) Continuation of application No. 11/997,413, filed as application No. PCT/JP2006/315103 on Jul. 31, 2006, now abandoned.

(30) Foreign Application Priority Data

Aug. 1, 2005 (JP) ................. 2005-222749

(51) Int. Cl.
| | | |
|---|---|---|
| A61K 9/00 | (2006.01) | |
| A61K 39/39 | (2006.01) | |
| A61K 47/26 | (2006.01) | |
| A61K 39/00 | (2006.01) | |
| A61K 47/34 | (2006.01) | |
| A61K 47/10 | (2006.01) | |
| A61K 47/12 | (2006.01) | |

(52) U.S. Cl.
CPC ............. *A61K 39/39* (2013.01); *A61K 47/26* (2013.01); *A61K 9/006* (2013.01); *A61K 2039/54* (2013.01); *A61K 9/0009* (2013.01); *A61K 2039/541* (2013.01); *A61K 47/34* (2013.01); *A61K 2039/53* (2013.01); *A61K 47/10* (2013.01); *A61K 9/0014* (2013.01); *A61K 2039/55511* (2013.01); *A61K 9/0021* (2013.01); *A61K 47/12* (2013.01)
USPC .................................. 424/400; 424/278.1

(58) Field of Classification Search
USPC .................... 424/400, 278.1; 604/20, 22
See application file for complete search history.

(56) References Cited

U.S. PATENT DOCUMENTS

| | | | |
|---|---|---|---|
| 4,605,670 A | 8/1986 | Saito et al. ............... 514/619 | |
| 2003/0039667 A1 | 2/2003 | Jira et al. | |
| 2003/0099659 A1 | 5/2003 | Gizurarson et al. ........ 424/184.1 | |
| 2004/0024058 A1 | 2/2004 | Yamada et al. | |
| 2004/0028698 A1 | 2/2004 | Colau et al. .............. 424/202.1 | |
| 2004/0185055 A1 | 9/2004 | Glenn et al. .............. 424/184.1 | |
| 2005/0106226 A1 | 5/2005 | Cormier et al. | |
| 2005/0163787 A1 | 7/2005 | Gizurarson et al. | |
| 2006/0110433 A1 | 5/2006 | Terahara et al. ............. 424/448 | |

FOREIGN PATENT DOCUMENTS

| | | |
|---|---|---|
| JP | 60-013721 | 1/1985 |
| JP | 60-161918 | 8/1985 |
| JP | 05-112466 | 5/1993 |
| JP | 05-255112 | 10/1993 |
| JP | 10-500662 | 1/1998 |
| JP | 2001-517233 | 10/2001 |
| JP | 2002-512186 | 4/2002 |
| JP | 2002-535100 | 10/2002 |
| JP | 2004-504120 | 2/2004 |
| JP | 2004-526757 | 9/2004 |
| JP | 2004-528900 | 9/2004 |
| JP | 2004-538048 | 12/2004 |
| WO | WO 95/22989 | 8/1995 |
| WO | WO 9833474 A1 * | 8/1998 |
| WO | WO 98/42375 | 10/1998 |
| WO | WO 99/53912 | 10/1999 |
| WO | WO 00/44438 | 8/2000 |
| WO | WO 01/21207 A2 | 3/2001 |
| WO | WO 01/76608 | 10/2001 |
| WO | WO 02/07813 | 1/2002 |
| WO | WO 02/083058 | 10/2002 |
| WO | WO 02/085446 | 10/2002 |
| WO | WO 02/085447 | 10/2002 |
| WO | WO 2005/016440 | 2/2005 |

OTHER PUBLICATIONS

Abimosleh et al., Evidence-Based Complementary and Alternative Medicine, vol. 2013, Article ID 429706, 10 pages.*

Higo, Masato, "Butsuriteki Keihi Kyushu Sokushinho Iontophoresis no kaihatsu Doko", Journal of Pharmaceutical Science and Technology 2005 65(2):93-97 with abridged English translation.

(Continued)

*Primary Examiner* — Michael G Hartley
*Assistant Examiner* — Robert Cabral
(74) *Attorney, Agent, or Firm* — Licata & Tyrrell P.C.

(57) ABSTRACT

An adjuvant for transdermal or transmucosal administration which comprises at least one substance selected from an aliphatic alcohol, a free fatty acid and a fatty acid derivative but does not contain a substance represented by the following formula: wherein $R^3$ and $R^4$ may together form a cyclic ring, and $R^1$ and $R^2$ independently represent an alkyl side chain having 1 to 16 carbon atoms.

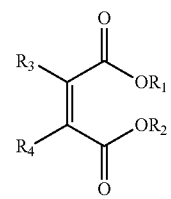

20 Claims, 4 Drawing Sheets

(56) References Cited

OTHER PUBLICATIONS

Harada et al., "I DDS Soron 5 Nippon Igai no Kuni de Jitsuyoka sareteiru DDS Seizai", DDS no Shinpo 1995 34-43 with abridged English translation.

Aungst et al., "Enhancement of naloxone penetration through human skin in vitro using fatty acids, fatty alchohols, surfactants, sulfoxides and amides", International Journal of Pharmaceutics 1986 33:225-234.

Seki et al., "Enhancing effects of medium chain aliphatic alcohols and esters on the permeation of 6-carboxyfluorescein and indomethacin through rat skin", Drug Delivery 2003 10:289-293.

Lyons et al, "A TCR Binds to Antagonist Ligands with Lower Affinities and Faster Dissociation Rates that to Agonist," Immunity, vol. 5, 53-61, Jul. 1996.

First office Action for U.S. Appl. No. 12/524,748, Aug. 29, 2011.

Office Communication from U.S. Appl. No. 12/524,748 dated Aug. 29, 2011.

Office Communication from U.S. Appl. No. 12/524,748 dated May 9, 2012.

* cited by examiner

ADJUVANT OR PHARMACEUTICAL PREPARATION FOR TRANSDERMAL OR TRANSMUCOSAL ADMINISTRATION

This patent application is a continuation of U.S. application Ser. No. 11/997,413, filed Mar. 7, 2008 now abandoned, which is the National Stage of International Application No. PCT/JP2006/315103 filed Jul. 31, 2006, which claims the benefit of priority from Japanese Application No. 2005-222749 filed Aug. 1, 2005, each of which are herein incorporated by reference in their entirety.

TECHNICAL FIELD

The present invention relates to a safe and efficient adjuvant for enhancing cutaneous immune activity, and to a pharmaceutical preparation for mainly transdermal or transmucosal administration.

BACKGROUND ART

The skin is formed from the stratum corneum, which is the outermost layer, the epidermis, the dermis, and subcutaneous tissue connective tissue, and the stratum corneum, which is formed from a dead cell layer and a lipid bilayer, normally shows a strong barrier function toward many materials. In the epidermal layer, antigen-presenting cells called Langerhans' cells are present and carry out an immune function. Mucous membranes, which cover the oral cavity, the nasal cavity, respiratory organs, digestive organs, and genital organs, are also a boundary with the external environment and have the same structure as that of the skin except that there is no stratum corneum, which is the outermost layer of the skin. Mucous membranes are in contact with various types of foreign substances during food ingestion, breathing, etc., and are a main route for, for example, pathogenic microorganisms to enter the interior of a host body. Because of this, the immunological defense mechanism in the mucous membrane is also important as a biological barrier.

Langerhans' cells capture a protein antigen that has entered the interior of the skin, decompose it internally, and express a peptide fragment on an MHC molecule. The MHC-peptide complex moves from an afferent lymphatic vessel to a subcortical layer of a regional lymph node and contacts a T cell via an interdigitating cell. Due to the Langerhans' cells moving in this way, the antigen is efficiently transmitted from the skin to $T_H$ cells present within the lymph node. Langerhans' cells have an abundance of MHC class II molecules, which are necessary for presenting an antigen to the $T_H$ cells.

An adjuvant is a material that enhances immunogenicity, and when it is administered with an antigen, the response to the antigen increases. In vaccination, an adjuvant is useful from the viewpoint of reduction in the vaccine dose and the number of times of administration. There has been a large amount of research into adjuvants, and as some examples an aluminum salt, an immune-stimulating complex (ISCOM), a bacteria-derived material, etc. are known. However, many of these adjuvants are directly administered subcutaneously or intramuscularly, and in such a case a tissue disorder such as contact hypersensitivity, subcutaneous nodules, or granuloma is induced. There is therefore a high demand for a safe and efficiently administrable adjuvant and preparation in immunostimulation such as human vaccination.

With regard to the adjuvant, a large number of vaccine formulations that contain an attenuated pathogen or protein subunit antigen have been developed so far. In most cases, the conventional vaccine preparations contain an adjuvant for enhancing the immune response. For example, an adjuvant forming a depot (Depot) is well known. This adjuvant makes an administered antigen be absorbed or precipitated, thus forming a depot at the injection site. Typical examples of the depot-forming adjuvant include an aluminum compound such as aluminum phosphate or aluminum hydroxide gel and an oil-in-water emulsion.

However, although the depot-forming adjuvant enhances the antigenicity, since it causes a local tissue disorder such as erythema, contact hypersensitivity, or granuloma formation when it is administered subcutaneously or intramuscularly, there is a problem in terms of application. Furthermore, in transdermal administration, there is a problem with the absorbability of an aluminum salt. Such problems with transdermal absorbability of the adjuvant itself are also common problems for an immune-stimulating complex (ISCOM), a bacteria-derived material, or a cytokine as an adjuvant. For example, it is known that muramyldipeptide causes, when injected, a pyretic reaction having symptoms similar to those of influenza, Reiter's syndrome, general joint pain, in some cases anterior uveitis, arthritis, or urethritis.

As hereinbefore described, adjuvants often cause severe local tissue disorder when subcutaneously or intramuscularly administered. In order to avoid this local tissue disorder, transdermal administration has been considered, but conventional adjuvants are either macromolecules, for example, an immune-stimulating complex (ISCOM), a bacteria-derived material, etc., or an aluminum compound, etc., none of which are compounds that are suitable for transdermal administration.

Moreover, in recent years, as means for enhancing permeation, external administration employing iontophoresis or a device equipped with microneedles has been investigated, but if, in addition to an antigen, which is a macromolecule, the adjuvant also has poor absorbability, it is currently impossible to make the antigen and the adjuvant permeate efficiently.

For example, Patent Publication 1 discloses iontophoresis as a method for delivering a macromolecular antigen to the interior of a skin cell, but there is no description of an adjuvant.

Patent Publication 2 discloses a skin patch having a microprojection array and a reservoir containing an antigen agonist and an immune response-enhancing adjuvant, and its application method for vaccination of an animal (e.g. man). However, the adjuvants described in this publication are limited to metal salts and macromolecules (peptides, etc.), and there is no description of an adjuvant having skin permeability.

Patent Publication 3 discloses, as a low molecular weight adjuvant to be administered by injection, a long chain aliphatic alcohol, an ester thereof with a $C_1$ to $C_6$ alkanoic acid, and a specific ester of a long chain fatty acid, an alkanol, and a polyol, but there is no description of the immune response thereof toward an antigen by transdermal administration.

Moreover, Patent Publication 4 discloses a local administration method that includes a step of administering a mixture of an antigen and an oleophilic solvent, and a step of administering, after the above administration, a material for inducing migration of Langerhans' cells. However, in accordance with this publication, the material for promoting the induction for Langerhans' cells is limited to a divalent unsaturated carboxylic acid ester, such as dibutyl phthalate, represented by the formula below.

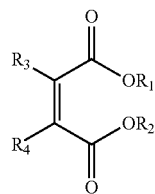

[Chem. 1]

(in the formula, $R_3$ and $R_4$ may be bonded to form a cyclic ring, and $R_1$ and $R_2$ are independently an alkyl side chain containing 1 to 16 carbon atoms).

Patent Publication 5 discloses a dry preparation containing cholera toxin or a related ADP-ribosylation toxin as an adjuvant. In such a preparation, it is thought that the cholera toxin or related ADP-ribosylation toxin as an adjuvant permeates the skin and induces an immune response. On the other hand, there is little information on the safety of such adjuvants, and there are the defects of the permeability toward skin being low due to them being macromolecules and the cost being high.

[Patent Publication 1] JP, A, (PCT) 2002-535100
[Patent Publication 2] JP, A, (PCT) 2004-538048
[Patent Publication 3] JP, A, (PCT) 2004-526757
[Patent Publication 4] JP, A, (PCT) 2002-512186
[Patent Publication 5] JP, A, (PCT) 2001-517233

As described above, conventional adjuvants used for injection have problems such as local tissue disorders. Furthermore, transdermal absorption preparations are characterized by excellent safety and simplicity compared with an injection, but there are very few materials, in particular low molecular weight compounds, that efficiently exhibit the action of a transdermally administered adjuvant. Moreover, in the clinical field there is a strong desire for an adjuvant that can be provided at low cost.

DISCLOSURE OF INVENTION

Problems to be Solved by the Invention

It is therefore an object of the present invention to provide a low molecular weight adjuvant that can be safely administered by transdermal or transmucosal administration without causing skin irritation, etc., and that efficiently enhances the immunogenicity of an antigen, and to provide a preparation thereof.

Means for Solving the Problems

While carrying out an intensive investigation in order to solve the above problems, it has surprisingly been found by the present inventors that some types of low molecular weight compound not only exhibit a strong immune enhancing effect in transdermal or transmucosal administration but also avoid skin irritation and tissue disorders, and as a result of further research, the present invention has been accomplished.

That is, the present invention relates to an adjuvant for transdermal or transmucosal administration, the adjuvant containing at least one selected from aliphatic alcohols, free fatty acids, and fatty acid derivatives but not containing one represented by the formula below.

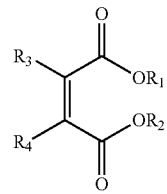

[Chem. 2]

(In the formula, $R_3$ and $R_4$ may be bonded to form a cyclic ring, and $R_1$ and $R_2$ are independently an alkyl side chain containing 1 to 16 carbon atoms.)

Furthermore, the present invention relates to the adjuvant, wherein at least one of the aliphatic alcohols is a saturated or unsaturated straight-chain or branched alcohol having 8 to 20 carbons.

Moreover, the present invention relates to the adjuvant, wherein at least one of the aliphatic alcohols is lauryl alcohol, oleyl alcohol, isostearyl alcohol, octyldodecanol, or decanol.

Furthermore, the present invention relates to the adjuvant, wherein at least one of the fatty acid derivatives is a fatty acid ester.

Moreover, the present invention relates to the adjuvant, wherein at least one of the fatty acid esters has a fatty acid carbon number of 10 to 20 and a degree of unsaturation of the fatty acid of 0 or 1.

Furthermore, the present invention relates to the adjuvant, wherein at least one of the fatty acid esters is a monovalent fatty acid ester.

Moreover, the present invention relates to the adjuvant, wherein at least one of the monovalent fatty acid esters is sorbitan monolaurate, propylene glycol monolaurate, isopropyl myristate, sorbitan monooleate, glycerol monooleate, cetyl palmitate, or oleyl oleate.

Furthermore, the present invention relates to the adjuvant, wherein at least one of the free fatty acids is a saturated or unsaturated straight-chain or branched fatty acid having 8 to 20 carbons.

Moreover, the present invention relates to the adjuvant, wherein at least one of the free fatty acids is oleic acid, linoleic acid, γ-linolenic acid, linolenic acid, lauric acid, stearic acid, or palmitic acid.

Furthermore, the present invention relates to a pharmaceutical preparation that includes any of the adjuvants above.

Moreover, the present invention relates to the pharmaceutical preparation, wherein it further includes at least one type of antigen.

Furthermore, the present invention relates to the pharmaceutical preparation, wherein it is used in transdermal or transmucosal administration.

Moreover, the present invention relates to the pharmaceutical preparation, wherein it is at least one type of an ointment, a cream, a powder, a gel, a suppository, a poultice, a patch preparation, a lotion, a liquid, and a liniment.

Furthermore, the present invention relates to the pharmaceutical preparation, wherein it is a matrix type or layer type tape preparation or a reservoir type patch preparation.

Moreover, the present invention relates to the pharmaceutical preparation, wherein it is applied to intact skin or mucous membrane or physically or chemically treated skin or mucous membrane.

Furthermore, the present invention relates to the pharmaceutical preparation, wherein the physical or chemical treatment involves at least one of laser irradiation, skin abrasion, and microneedle, thermal, ultrasonic, electric field, magnetic field, pressure, and alkali treatments.

Moreover, the present invention relates to the pharmaceutical preparation, wherein it is applied by at least one of skin abrasion, microneedle, and needle-free injection.

Furthermore, the present invention relates to the pharmaceutical preparation, wherein part or the whole surface of a needle portion of a microneedle is coated with an antigen and/or an adjuvant.

Moreover, the present invention relates to the pharmaceutical preparation, wherein it is applied by at least one of hydration, denaturing, pore formation, exfoliation, bypass formation, and change in lamellar structure of the stratum corneum.

Furthermore, the present invention relates to the pharmaceutical preparation, wherein it is applied by at least one of iontophoresis, sonophoresis, or electroporation.

The present invention safely enhances the immunogenicity of an antibody by the use as an adjuvant of an aliphatic alcohol, a fatty acid, or a fatty acid derivative, which are not known to have adjuvant activity by transdermal administration. The adjuvant of the present invention generally has a lower molecular weight than that of conventional adjuvants, and can therefore be administered transdermally or transmucosally.

Effects of the Invention (1) In accordance with the adjuvant of the present invention, the immunogenicity of an antibody can be enhanced efficiently and safely by transdermal or transmucosal administration of a low molecular weight adjuvant.

(2) Among the adjuvants of the present invention, in accordance with the adjuvant in which at least one of the aliphatic alcohols is a saturated or unsaturated straight-chain or branched alcohol having 8 to 20 carbons, the immunogenicity of an antibody can be enhanced more efficiently and safely.

(3) Among the adjuvants of the present invention, in accordance with one in which at least one of the aliphatic alcohols is lauryl alcohol, oleyl alcohol, isostearyl alcohol, octyldodecanol, or decanol, the immunogenicity of an antibody can be enhanced yet more efficiently and safely.

(4) Among the adjuvants of the present invention, in accordance with one in which at least one of the fatty acid derivatives is a fatty acid ester, the immunogenicity of an antibody can be enhanced more efficiently and safely.

(5) Among the adjuvants of the present invention, in accordance with the adjuvant in which at least one of the fatty acid esters has a fatty acid carbon number of 10 to 20 and a degree of unsaturation of the fatty acid of 0 or 1, the immunogenicity of an antibody can be enhanced yet more efficiently and safely.

(6) Among the adjuvants of the present invention, in accordance with one in which at least one of the fatty acid esters is a monovalent fatty acid ester, the immunogenicity of an antibody can be enhanced still more efficiently and safely.

(7) Among the adjuvants of the present invention, in accordance with one in which at least one of the monovalent fatty acid esters is sorbitan monolaurate, propylene glycol monolaurate, isopropyl myristate, sorbitan monooleate, glycerol monooleate, cetyl palmitate, or oleyl oleate, the immunogenicity of an antibody can be enhanced particularly efficiently and safely.

(8) Among the adjuvants of the present invention, in accordance with one in which at least one of the free fatty acids is a saturated or unsaturated straight-chain or branched fatty acid having 8 to 20 carbons, the immunogenicity of an antibody can be enhanced more efficiently and safely.

(9) Among the adjuvants of the present invention, in accordance with one in which at least one of the free fatty acids is oleic acid, linoleic acid, γ-linolenic acid, linolenic acid, lauric acid, stearic acid, or palmitic acid, the immunogenicity of an antibody can be enhanced yet more efficiently and safely.

(10) In accordance with the pharmaceutical preparation of the present invention, the immunogenicity of an antibody can be enhanced more simply.

(11) Among the pharmaceutical preparations of the present invention, in accordance with one that further includes at least one type of antigen, the immunogenicity of an antibody can be enhanced more simply and efficiently.

(12) Among the pharmaceutical preparations of the present invention, in accordance with one that is used in transdermal or transmucosal administration, the immunogenicity of an antibody can be enhanced yet more simply and efficiently.

(13) Among the pharmaceutical preparations of the present invention, in accordance with one that is at least one type of an ointment, a cream, a powder, a gel, a suppository, a poultice, a patch preparation, a lotion, a liquid, and a liniment, the immunogenicity of an antibody can be enhanced still more simply and efficiently.

(14) Among the pharmaceutical preparations of the present invention, in accordance with one that is a matrix type or layer type tape preparation or a reservoir type patch preparation, delivery of the adjuvant is carried out more efficiently and/or over a long period of time.

(15) Among the pharmaceutical preparations of the present invention, in accordance with one that is applied to intact skin or physically or chemically treated skin or mucous membrane, delivery of the adjuvant is carried out more quickly.

(16) Among the pharmaceutical preparations of the present invention, in accordance with one in which the physical or chemical treatment involves at least one of laser irradiation, skin abrasion, and microneedle, thermal, ultrasonic, electric field, magnetic field, pressure, and alkali treatments, delivery of the adjuvant is carried out yet more quickly.

(17) Among the pharmaceutical preparations of the present invention, in accordance with one that is applied by at least one of skin abrasion, microneedle, and needle-free injection, the effects of the pharmaceutical preparation can be enhanced.

Among the pharmaceutical preparations of the present invention, in accordance with one in which part or the whole surface of a needle portion of a microneedle is coated with an antigen and/or an adjuvant, it is possible to accomplish a more useful and highly safe immune response to an antigen.

(18) Among the pharmaceutical preparations of the present invention, in accordance with one that is applied by at least one of hydration, denaturing, pore formation, exfoliation, bypass formation, and change in lamellar structure of the stratum corneum, transdermal absorption of the adjuvant is promoted, and the effect thereof, that is, enhancement of the immunogenicity of an antibody, can be exhibited more efficiently and safely.

(19) Among the pharmaceutical preparations of the present invention, in accordance with one that is applied by at least one of iontophoresis, sonophoresis, and electroporation, absorption of the adjuvant is carried out more efficiently, and the effect thereof can be exhibited yet more efficiently and safely.

As hereinbefore described, in accordance with the present invention, there is provided an adjuvant that has a strong immune enhancing effect in transdermal or transmucosal administration and that is safe without giving skin irritation or tissue disorder. Furthermore, the adjuvant and the preparation thereof of the present invention may be used together with an antigen, that is, it is also possible to enhance the immune activity of the antigen effectively in transdermal or transmucosal administration involving a method employing a device such as iontophoresis, electroporation, or sonophoresis (ultrasonic waves), or involving a microcannula, microneedles, etc. Moreover, since the adjuvant for transdermal or transmucosal absorption of the present invention has a low melting point and a low molecular weight, high transdermal or transmucosal absorbability is shown, it can be applied to various types of transdermal absorption preparations, for example, a liquid, a patch, an ointment, a gel, a cream, a lotion, etc., and it can be provided at low cost.

BEST MODE FOR CARRYING OUT THE INVENTION

One of the components that can be contained in the adjuvant of the present invention is selected from aliphatic alcohols. In such aliphatic alcohols, straight-chain or branched aliphatic alcohols are preferable. In such aliphatic alcohols, the number of carbons and the molecular weight are not particularly limited, but from the viewpoint of skin permeability, they preferably have 8 to 20 carbons. Furthermore, such aliphatic alcohols may be either saturated or unsaturated.

Such aliphatic alcohols are for example octyldodecanol, lauryl alcohol, oleyl alcohol, isostearyl alcohol, decanol, etc.; among them lauryl alcohol, octyldodecanol, and isostearyl alcohol are particularly preferably, and lauryl alcohol is most preferable.

Another component that can be contained in the adjuvant of the present invention is selected from fatty acid derivatives. The 'fatty acid derivatives' referred to in the present invention means compounds containing a fatty acid moiety, and typical examples thereof include fatty acid esters, fatty acid amides, and fatty acid halides. Among these fatty acid derivatives, fatty acid esters are preferable, and fatty acid esters and monovalent fatty acid esters having a fatty acid carbon number of 10 to 20 and a degree of unsaturation of the fatty acid of 0 or 1 are more preferable.

Examples of such fatty acid esters include sorbitan monolaurate, propylene glycol monolaurate, sorbitan monooleate, isopropyl myristate, polyethylene glycol, glycerol monooleate, cetyl palmitate, and oleyl oleate, and in particular sorbitan monolaurate is most preferable.

Yet another component that can be contained in the adjuvant of the present invention is selected from free fatty acids. Among such free fatty acids, those having 8 to 20 carbons are preferable. Such fatty acids may be either saturated or unsaturated and either straight-chain or branched. Preferred examples of the free fatty acids include oleic acid, linoleic acid, γ-linolenic acid, linolenic acid, lauric acid, stearic acid, and palmitic acid. Oleic acid and lauric acid are particularly preferable.

The adjuvants of the present invention may be used either singly or in combination. In particular when there is a synergistic effect between the adjuvants, they may be used in combination. In other cases, they may be used singly or may be used in combination according to the intended purpose.

The adjuvant of the present invention can exhibit an effect simply by transdermal or transmucosal administration. Therefore, by making a conventionally used transdermal administration preparation contain the adjuvant of the present invention, it becomes possible to carry out noninvasive internal administration with an external use form pharmaceutical preparation. With regard to the form of such a pharmaceutical preparation, it is not particularly limited as long as it is a preparation form that contains the adjuvant of the present invention and the adjuvant can be administered transdermally, and it may be selected as necessary from a poultice, a patch preparation, an ointment, a cream, a liquid, a gel, a lotion, etc. In the present specification, the patch preparation includes a matrix type or layer type tape preparation and a reservoir type patch preparation.

Furthermore, such a transdermally or transmucosally administered preparation may be produced by a standard method using the adjuvant of the present invention in combination with, as a base, any component such as a solubilizing agent, a solubilizing adjuvant, a pH adjusting agent, an antiseptic, an absorption accelerator, a stabilizer, a filler, a thickening agent, a pressure sensitive adhesive, or a wetting agent. Moreover, among the pharmaceutical preparations of the present invention, another form of pharmaceutical preparation may be produced by a standard method.

For example, among the base components in the transdermally or transmucosally administered preparation of the present invention, the thickening agent is preferably one that can stably retain 30% to 80% moisture and has water holding capacity. Water-soluble polymers, etc. are suitably used, and specific examples thereof include vegetable-based natural polymers such as guar gum, locust bean gum, carrageenan, alginic acid, sodium alginate, agar, gum arabic, tragacanth gum, karaya gum, pectin, and starch; microbial-based natural polymers such as xanthan gum and acacia gum; animal-based natural polymers such as gelatin and collagen; cellulose-based semisynthetic polymers such as methyl cellulose, ethyl cellulose, hydroxyethyl cellulose, and sodium carboxymethyl cellulose; starch-based semisynthetic polymers such as soluble starch, carboxymethyl starch, and dialdehyde starch; vinyl-based synthetic polymers such as polyvinyl alcohol, polyvinylpyrrolidone, and polyvinyl methacrylate; acrylic-based synthetic polymers such as polyacrylic acid and sodium polyacrylate; and other synthetic polymers such as polyethylene oxide and methylvinyl ether/maleic anhydride copolymer. Sodium polyacrylate is particularly preferable. This is because it has a high gel strength and excellent water holding capacity. Furthermore, a sodium polyacrylate having an average degree of polymerization of 20000 to 70000 is preferable. As the average degree of polymerization becomes less than 20000, a tendency is exhibited for the thickening effect to become poor and for a sufficient gel strength not to be obtained, and as the average degree of polymerization becomes greater than 70000, a tendency is exhibited for the thickening effect to become too strong and for the workability to be degraded, neither being desirable. Furthermore, by the use of the above-mentioned water-soluble polymers in a combination of two or more types, for example, a polymeric complex may be formed with the strongly ionic polymer sodium polyacrylate, thus giving an elastic gel having a higher gel strength.

With regard to the wetting agent, a polyhydric alcohol such as glycerol, propylene glycol, or sorbitol, etc. may be added, and with regard to the filler, kaolin, zinc oxide, talc, titanium, bentonite, aluminum silicate, titanium oxide, zinc oxide, aluminum metasilicate, calcium sulfate, calcium phosphate, etc. may be added. Furthermore, with regard to the solubilizing adjuvant or absorption accelerator, propylene carbonate, crotamiton, 1-menthol, peppermint oil, limonene, diisopropyl adipate, etc. may be added, and as a medicinal adjuvant, methyl salicylate, glycol salicylate, 1-menthol, thymol, peppermint oil, nonanoic acid vanillylamide, red pepper extract, etc. may be added. Moreover, a stabilizer, an antioxidant, an emulsifier, a surfactant, etc. may be added as necessary.

The surfactant in the present invention may be either a nonionic surfactant or an ionic surfactant (cationic, anionic, amphoteric), but from the viewpoint of safety is desirably a nonionic surfactant that is normally used as a pharmaceutical base. Specific examples thereof include a sugar alcohol fatty acid ester such as a sucrose fatty acid ester, a sorbitan fatty acid ester, a glycerol fatty acid ester, a polyglycerol fatty acid ester, a propylene glycol fatty acid ester, a polyoxyethylene sorbitan fatty acid ester, a polyoxyethylene glycerol fatty acid ester, a polyethylene glycol fatty acid ester, a polyoxyethylene castor oil, and a polyoxyethylene hardened castor oil.

The transdermal administration preparation of the present invention may further contain a crosslinking agent, a polymerization agent, etc. as necessary. A plaster may be strengthened and made to have water holding capacity. The crosslinking agent or polymerization agent is selected as appropriate according to the type of thickening agent, etc. For example, when a polyacrylic acid or a polyacrylic acid salt is used as the thickening agent, a compound having at least two epoxy groups in the molecule or a polyvalent metal compound is preferably used, examples of the polyvalent metal compound including an inorganic acid salt such as a hydrochloride, a sulfate, a phosphate, or a carbonate, or an organic acid salt such as a citrate, a tartarate, a gluconate, or a stearate of Ca, Mg, Al, etc., an oxide such as zinc oxide or silicic anhydride, and a hydroxide such as aluminum hydroxide or magnesium hydroxide. Furthermore, when polyvinyl alcohol is used as the thickening agent, adipic acid, thioglycolic acid, an epoxy compound (epichlorohydrin), an aldehyde, an N-methylol compound, a complex such as a compound of Al, Ti, Zr, Sn, V, Cu, B, Cr, etc. are suitably used. Moreover, when polyvinylpyrrolidone is used as the thickening agent, a methylvinyl ether/maleic anhydride copolymer, a polyacid compound (polyacrylic acid, tannic acid, or a derivative thereof) or an alkali metal salt thereof, etc. are suitably used. Furthermore, when polyethylene oxide is used as the thickening agent, a peroxide, a polysulfonazide, etc. are desirably used.

Furthermore, when a methylvinyl ether/maleic anhydride copolymer is used as the thickening agent, a polyfunctional hydroxy compound, a polyamine, iodine, gelatin, polyvinylpyrrolidone, an iron, mercury, lead salt, etc. are suitably used. When gelatin is used as the thickening agent, an aldehyde such as formaldehyde, glutaraldehyde, or dialdehyde starch, glyoxal, a diepoxide such as butadiene oxide, a diketone such as divinyl ketone, a diisocyanate, etc. are suitably used. Furthermore, when sodium polyacrylate is used as the thickening agent, it is preferable to add as the crosslinking agent a polyvalent metal salt such as lithium hydroxide, zinc hydroxide, aluminum hydroxide, or sodium borate. In particular, a zinc salt and an aluminum salt are preferable. This is because a crosslinking reaction is promoted. The concentration of polyvalent metal salt added as the crosslinking agent is preferably 0.5 to 1.5 equivalents relative to 1 equivalent of the thickening agent (or the water-soluble polymer). By setting the concentration of the polyvalent metal salt so as to be at least 0.5 equivalents, the reaction is promoted and the gel strength increases, and by setting the concentration of a polyvalent metal salt so as to be no greater than 1.5 equivalents, the reaction proceeds at an appropriate speed, thus carrying out uniform gelling and thereby improving the workability.

When an adjuvant is added to the pharmaceutical preparation, the amount thereof added is not particularly limited. The amount added may be such that a concentration of adjuvant sufficient for the effect of the adjuvant to be exhibited is noninvasively absorbed into the body. With regard to the adjuvant of the present invention, the adjuvant may be suitably used on its own, but it is also preferable to add it to the preparation at 0.1 to 99 wt %, more preferably 5 to 90 wt %, and particularly preferably 10 to 80 wt %. It is most preferably 15 to 75 wt %.

Furthermore, the adjuvant of the present invention may be administered into the body together with an antigen. In this case, if the antigen can be transdermally administered, it may be formed into a transdermal noninvasive preparation containing the adjuvant and the antigen. With regard to the form of the transdermal administration preparation, a poultice, a patch preparation, an ointment, a cream, a liquid, a gel, a lotion, etc. may be selected as necessary, and there are no particular limitations as long as it is a form containing an antigen and a low molecular weight adjuvant and can be administered transdermally. As described above, the patch preparation in the present specification includes matrix type and layer type tape preparations and a reservoir type patch preparation. Such transdermal preparations may also be produced by a standard method by using as a base any component such as a solubilizing agent, a solubilizing adjuvant, a pH adjusting agent, an antiseptic, an absorption accelerator, a stabilizer, a filler, a thickening agent, or a pressure sensitive adhesive, and by combining it with an antigen and the adjuvant of the present invention. The base may contain as the absorption accelerator one that enhances the skin permeability of the adjuvant and/or antigen, but even without such an absorption accelerator being contained, the adjuvant of the present invention can enhance the immunogenicity of the antigen.

On the other hand, when the antigen used in combination does not have sufficient transdermal activity, the adjuvant of the present invention may be transdermally administered, and the antigen used in combination may be non-transdermally administered.

The amounts of antigen and adjuvant added in the combination preparation containing the antigen and the adjuvant may be determined as appropriate according to the combination of antigen and adjuvant. The content of the adjuvant in such a preparation is not particularly limited, and it may be an amount that induces a sufficient antigen immune response by a transdermal route. It is therefore preferable for the adjuvant of the present invention to be added at 0.1 to 99 wt % to the combination preparation containing the antigen and the adjuvant, more preferably 5 to 90 wt %, and particularly preferably 10 to 80 wt %. The most preferred content of the adjuvant in the preparation is 15 to 75 wt %.

The antigen used here is not particularly limited, and examples thereof include polynucleotides (DNA vaccine, RNA vaccine) and protein-based vaccines. Specific examples thereof include proteins, polysaccharides, oligosaccharides, lipoproteins, attenuated or killed viruses such as cytomegalovirus, hepatitis B virus, hepatitis C virus, human papillomavirus, rubella virus, and varicella zoster virus, attenuated or killed bacteria such as *Bordetella pertussis, Clostridium tetani, Corynebacterium diphtheriae*, group A Streptococci, *Legionella pneumophila, Neisseria meningitidis, Pseudomonas aeruginosa, Streptococcus pneumoniae, Treponema pallidum*, and *Vibrio cholerae*, and mixtures thereof. A large number of commercially available vaccines containing an antigenically active substance may also be used in the present invention. These include influenza vaccine, Lyme disease vaccine, rabies vaccine, measles vaccine, mumps vaccine, chicken pox vaccine, smallpox vaccine, hepatitis vaccine, whooping cough vaccine, and diphtheria vaccine and, in addition, antigens used in vaccine treatments for cancer, arteriosclerosis, neurological disorders, Alzheimer's, etc. Furthermore, this antigen may be an allergenic substance having antigenicity (sensitization), and a large variety of metals and chemical substances correspond thereto. For example, when an allergy test for clarifying an antigen for atopic dermatitis or a treatment is carried out, house dust such as dust or inactivated mites or various types of pollen may be used. Examples also include antigens recognized by inflammatory T cells related to T cell-mediated autoimmune diseases or symptoms.

The route of administration of these antigens is not particularly limited, and examples thereof include oral and injection (intramuscular, subcutaneous, intradermal) methods of administration, and transmucosal or transdermal administration. In the case of transdermal administration, transdermal administration means is selected that is commensurate with the skin permeability of the antigen and the amount of antigen required to be administered.

By administering the adjuvant of the present invention by the same means as used for the antigen or by a different transdermal administration means, Langerhans' cells of the skin are activated and they are efficiently transmitted from the skin to $T_H$ cells present within the lymph node, thus accomplishing a high immune response. This makes possible a simple evaluation of the antigenicity of external medications, cosmetics, and allergenic substances, the prevention and treatment of infectious diseases, cancers, allergy, etc. by vaccine, and the treatment of T cell-mediated autoimmune diseases.

For the purpose of further improving the transdermal absorbability, the adjuvant preparation of the present invention or a preparation containing the adjuvant and an antigen at the same time may be subjected to a method involving application after a skin abrasion treatment or employing a device such as iontophoresis, electroporation, sonophoresis (ultrasonic waves) or involving a transdermal administration mode employing a device equipped with a microcannula, microneedles, etc., thus enabling a more useful and higher safety immune response toward an antigen to be accomplished. Moreover, the above-mentioned administration modes are not particularly limited, and optimum administration means may be selected according to the skin permeability of the antigen or the amount of antigen required to be administered.

It is preferable to employ a method in which part or the whole surface of a needle portion of a microneedle is coated with an antigen and/or an adjuvant together with a carrier. In this case, it is not always necessary to apply the adjuvant by coating, and it may be applied to the skin in advance.

For example, coating of a needle portion of a microneedle is described in JP, A, (PCT) 2004-504120, JP, A, (PCT) 2004-528900, WO 2005/016440, etc.

EXAMPLES

Example 1

The abdomen of 7 to 8 W male BALB/c mice was shaved, and 50 uL of an acetone solution (50%) of a candidate adjuvant was transdermally administered. On the other hand, for a group for which an antigen hapten was used in combination, 50 uL of a 1:1 mixture of an FITC solution (5 mg/mL in acetone) and a solution of the adjuvant was transdermally administered to the abdomen. 5 days later, lymph node (cervix, groin) was removed, and the intensity of expression of MHC Class II molecules by lymph cells was analyzed by flow cytometry (FIG. 1).

As shown in FIG. 1, in transdermal administration with a low molecular weight adjuvant such as a free fatty acid (oleic acid), a fatty acid ester (sorbitan monolaurate, sorbitan monooleate), or an aliphatic alcohol (lauryl alcohol, oleyl alcohol, isostearyl alcohol), a remarkable increase in lymph cell count was observed. That is, it was confirmed that a low molecular weight free fatty acid, a fatty acid ester, and an aliphatic alcohol have a high adjuvant effect in transdermal administration. In particular, lauryl alcohol showed the most outstanding adjuvant effect.

Example 2

A group for which the abdomen of 7 to 8 W male BALB/c mice was shaved and 25 uL of candidate adjuvant (undiluted) was intradermally administered and a group for which 50 uL of an acetone solution (50%) was transdermally administered were scored for skin irritation (Table 1).

As shown in Table 1, it was confirmed that transdermal administration of low molecular weight adjuvants such as fatty acid esters (polyethylene glycol monolaurate, sorbitan monolaurate) and aliphatic alcohols (lauryl alcohol, oleyl alcohol, isostearyl alcohol, octyldodecanol) did not cause skin irritation, and compared with intradermal administration there was minimal skin irritation.

TABLE 1

Skin Irritation Score (intradermal administration vs transdermal administration)

| | Skin irritation score | |
| --- | --- | --- |
| Skin irritation evaluation<br>Adjuvant | Intradermal<br>administration | Transdermal<br>administration |
| Lauryl alcohol | +++ | − |
| Oleyl alcohol | +++ | − |
| Isostearyl alcohol | ++ | − |
| Octyldodecanol | + | − |
| Polyethylene glycol monolaurate | ++ | − |
| Sorbitan monolaurate | ++ | − |

Example 3

The abdomen of 7 to 8 W male BALB/c mice was shaved, and the animals were divided into an untreated group and a group to which an antigen was intradermally administered. OVA was dissolved in physiological saline and adjusted to give 10 ug/head, and for an OVA-only group 25 uL of the OVA aqueous solution was intradermally administered. For groups in which there was combined use with various types of adjuvant, immediately after the OVA solution was intradermally administered, 25 uL of the adjuvant solution was transdermally administered (coated) via the skin surface of the abdomen. Administration was carried out at 0, 2, and 4 W, blood was collected at 2, 4, and 5 W, and the OVA-specific IgG antibody titer after 2, 4, and 5 W was measured by ELISA. The results of 5 W data are given in Table 2.

As shown in Table 2, when the change in antigen-specific IgG was examined employing in combination intradermal administration of the antigen ovalbumin and transdermal administration of various types of adjuvants to intact skin, a high antigen. IgG immune response was observed for all candidate adjuvants. Groups for which lauryl alcohol or oleyl alcohol was administered in combination showed the highest immune response. From these results, it was confirmed that the aliphatic alcohols not only enhance the transdermal absorbability of an antigen but they also have immunostimulatory activity as adjuvants.

TABLE 2

| Adjuvant | Antibody titer ($\times 10^4$) |
|---|---|
| Lauryl alcohol | 2.1 |
| Oleyl alcohol | 2.1 |
| Isostearyl alcohol | 1.3 |
| Octyldodecanol | 0.6 |
| Polyethylene glycol monolaurate | 0.9 |
| FCA (Freund's Complete Adjuvant) | 1.3 |
| None | 0.3 |

Example 4

The abdomen of 7 to 8 W male BALB/c mice was shaved, and the animals were divided into an untreated group, a microneedle group, a skin abrasion pretreatment group, and an iontophoresis group. OVA (ovalbumin antigen) was adjusted to give 100 ug/head, for an OVA-only group an OVA aqueous solution was applied, and for a group in which lauryl alcohol (LA) was used in combination, an emulsified solution formed by mixing the OVA solution, LA and Tween 20 (emulsifier) at 1:1:0.01 was used. For the microneedle group, the pre-shaved abdomen skin was punctured with 1 cm$^2$ of microneedles (needle length about 200 um, 400 needles/cm$^2$), and immediately after this 50 uL of the above-mentioned emulsion solution was applied. For the skin abrasion treatment group, instead of the microneedles, the skin was abraded 5 times with 3M RED Dot™ 2236 and 50 uL of the emulsion solution was applied. For the iontophoresis group, after the shaven abdomen skin was coated with 50 uL of the emulsion solution, an iontophoresis preparation (nonwoven cloth preparation: Ag, Ag/AgCl 1 cm$^2$) formed by impregnating a nonwoven cloth with physiological saline was affixed to the coated site, and direct current (0.4 mA/patch) was applied for 1 hour. Administration was carried out at 0, 2, and 4 W, blood was collected at 2, 4, and 5 W, and the OVA-specific IgG antibody titer was measured by ELISA. The results of 4 W data are shown in FIG. 2.

As shown in FIG. 2, when examining the change in antigen-specific IgG (4W) due to IP (iontophoresis), MN (microneedles), and Skin Prep (skin abrasion pretreatment) transdermal administration modes of the preparation containing ovalbumin antigen and/or lauryl alcohol, a high antigen IgG immune response was exhibited for all transdermal administration modes. Administering by means of iontophoresis showed the highest immune response. When lauryl alcohol was used in combination, a significant increase was observed for the antibody titer.

Example 5

OVA was adjusted to give 2 mg/patch, a needle portion of microneedles was coated with the antigen and 5% polyvinyl alcohol liquid, and for a microneedle group the abdomen of 7 to 8 W male hairless rats was punctured for 2 hours with physiological saline dropped onto the skin side. For a microneedle+lauryl alcohol group, LA was applied in advance, physiological saline was dropped onto the skin side, and it was punctured for 2 hours with microneedle needles coated with the antigen and 5% polyvinyl alcohol liquid. Administration was carried out at 0, 2, and 4 W, blood was collected at 2, 4, and 5 W, and the OVA-specific IgG antibody titer was measured by ELISA. The results are given in FIG. 3.

As shown in FIG. 3, when antigen-coated puncturing was carried out, the antibody titer did not increase, but when LA was applied, it increased, remarkably. The usefulness of the combined use of LA in antigen-coated microneedles was thus confirmed.

Example 6

OVA was adjusted to give 2 mg/patch, and for a microneedle group (OVA+5% polyvinyl alcohol), the abdomen of 7 to 8 W male hairless rats was punctured for 2 hours with a needle portion of microneedles coated with antigen and 5% polyvinyl alcohol liquid [mixed at antigen solution:10% polyvinyl alcohol=1:1]. Furthermore, for microneedle groups (OVA+olive oil) or (OVA+lauryl alcohol), microneedle needles were coated with an emulsion [antigen solution:olive oil or lauryl alcohol:surfactant (Tween 80)=1:1:0.01], and puncturing was carried out for 2 hours. Administration was carried out at 0, 2, and 4 W, blood was collected at 2, 4, and 5 W, and the OVA-specific IgG antibody titer was measured by ELISA. The results are shown in FIG. 4.

As shown in FIG. 4, when puncturing was carried out with microneedles coated with the antigen on its own or an emulsion of the antigen+olive oil (OLV), the antibody titer did not increase, but in the case of microneedles coated with lauryl alcohol it increased remarkably. The usefulness of coating the microneedles with the emulsion of the antigen+lauryl alcohol was thereby confirmed.

Example 7

OVA was adjusted to give 0.1 mg/patch, the abdomen of 7 to 8 W male BALB/c mice was shaved, and for a microneedle group (OVA) microneedle needles were coated with the antigen and 5% polyvinyl alcohol liquid [mixed at antigen solution:10% polyvinyl alcohol=1:1], and puncturing was carried out for 2 hours. Furthermore, for microneedle groups (OVA+lauryl alcohol or oleyl alcohol) microneedle needles were coated with an emulsion [antigen solution:olive oil or lauryl alcohol:surfactant (Tween 80)=1:1:0.01], and puncturing was carried out for 2 hours. Administering was carried out at 0, 2, and 4 W, blood was collected at 2, 4, and 5 W, and the OVA-specific IgG antibody titer was measured by ELISA. The results are given in FIG. 5.

As shown in FIG. 5, microneedles coated only with the antigen did not show a remarkable increase in the antibody titer, but when puncturing was carried out with microneedles coated with the antigen+lauryl alcohol or oleyl alcohol, the antibody titer increased remarkably. The usefulness of coating the microneedles with the emulsion of antigen+lauryl alcohol or oleyl alcohol was thereby confirmed.

Example 8

50 µL of an antigen (influenza H3N2: 1 µg/head) was administered dropwise to the nose of 7 to 8 W male BALB/c mice under inhalation anesthesia (sevoflurane) so as to match breathing. Antigen+LA [mixed at antigen solution:LA:surfactant (Tween 80)=9:1:0.05] was administered dropwise to the nose.

Furthermore, for an intradermal administration group, the abdomen was shaved under Nembutal anesthesia, and 50 µL of an antigen (influenza H3N2: 0.07 µg/head) was intradermally administered. The antigen+LA [mixed at antigen solution:LA: surfactant (Tween 80)=1:1:0.01] was intradermally administered. 2 and 4 weeks after the initial administration, boosting was carried out under the same conditions, blood was drawn from the fundus of the eye after 2, 4, and 5 weeks, and the antibody titer was measured. The results are shown in FIG. 6.

When an emulsion of the antigen and LA was administered transnasally, compared with the antigen on its own, the antibody titer increased. In the case of intradermal administration, the adjuvant effect of LA was observed as above.

Example 9

Confirmation of Effect of LA Adjuvant in Administration via Oral Mucous Membrane (Mouse)

25 uL at a time was administered twice to the mouth cavity of 7 to 8 W male BALB/c mice (OVA 2500 ug/head; in FIG. 7, which shows the results, '0' denotes a group of n=4 treated with a dosage of 50 uL [antigen solution], '20' denotes a group of n=2 treated with a dosage of 50 uL [mixed at antigen solution:LA:surfactant (Tween 80)=8:2:0.05], and '50' denotes a group of n=4 treated with a dosage of 50 uL [antigen solution:LA:surfactant (Tween 80)=5:5:0.05]). Boosting was carried out 1 week after the initial administration, blood was drawn from the fundus of the eye after 2 weeks, and the antibody titer was measured (in FIG. 7, — denotes the average value of the antibody titer obtained for each treatment group).

(Results)

When the antigen on its own or as two types of emulsions having varied LA concentrations were administered via the oral mucous membrane, in the case of the group with the antigen alone (0) the antibody titer did not increase, but in the case of the groups with the combined use of LA ((20) and (50)) the antibody titer increased in response to the LA concentration (FIG. 7). In the present example, it is surmised that parts of the antigen, LA, and surfactant were absorbed via the mucous membrane of the gastrointestinal tract, and primarily the mucous membrane of the intestinal tract, thus exhibiting an effect.

INDUSTRIAL APPLICABILITY

As described above, in accordance with the present invention, a safe and efficient low molecular weight adjuvant, selected from a fatty acid derivative or an aliphatic alcohol, and a transdermal administration preparation for enhancing cutaneous immune activity can be provided. That is, the adjuvant and the preparation of the present invention are transdermally administered, etc. as they are or are applied after abrading the skin, or are transdermally administered using iontophoresis, microneedles, etc., and they are widely used in this way for the evaluation of external medications, cosmetics, allergenic substances, or vaccine treatments, etc. of infections, cancer, arteriosclerosis, cranial nerve diseases such as Alzheimer's, allergies, etc. Furthermore, the present invention is also used as an anti-inflammatory immunomodulating substance for the treatment of T cell-mediated disease. The present invention therefore makes a great contribution to the pharmaceutical industry and its related industries.

Figure 1:
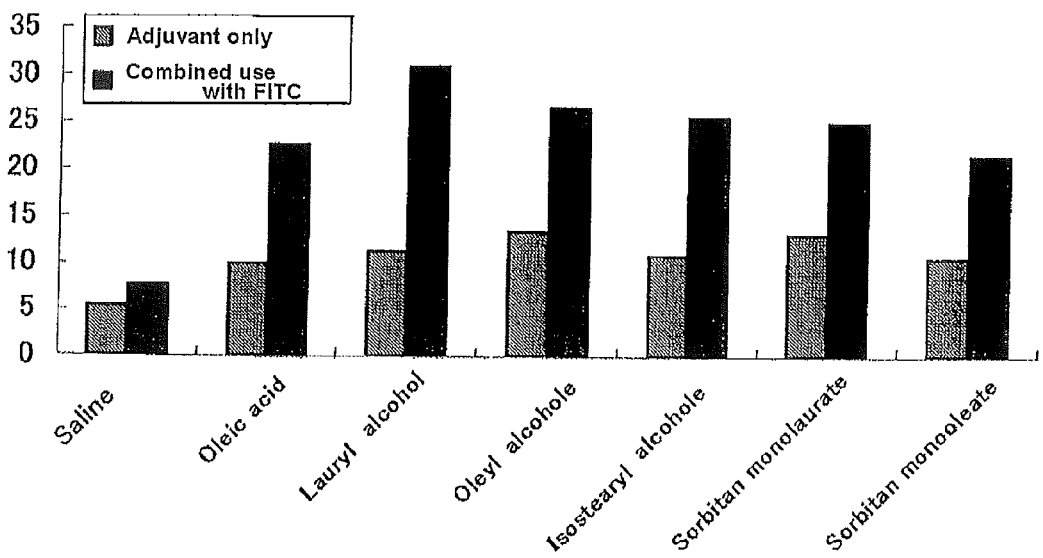
[FIG. 1] A diagram showing the effect of the adjuvant of the present invention on the intensity of expression of MHC-Class II molecules.
Figure 2:
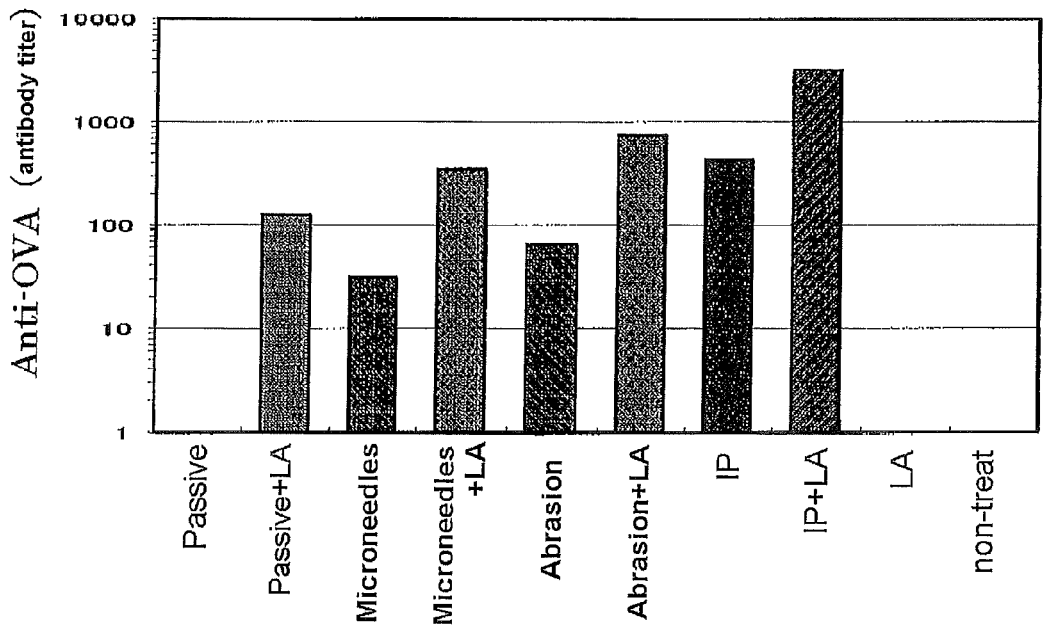
[FIG. 2] A diagram showing the effect of the adjuvant preparation of the present invention (containing lauryl alcohol) on the change in antigen-specific IgG of ovalbumin antigen (4W) in IP (iontophoresis), MN (microneedles), and Skin Prep (skin abrasion pretreatment).
Figure 3:
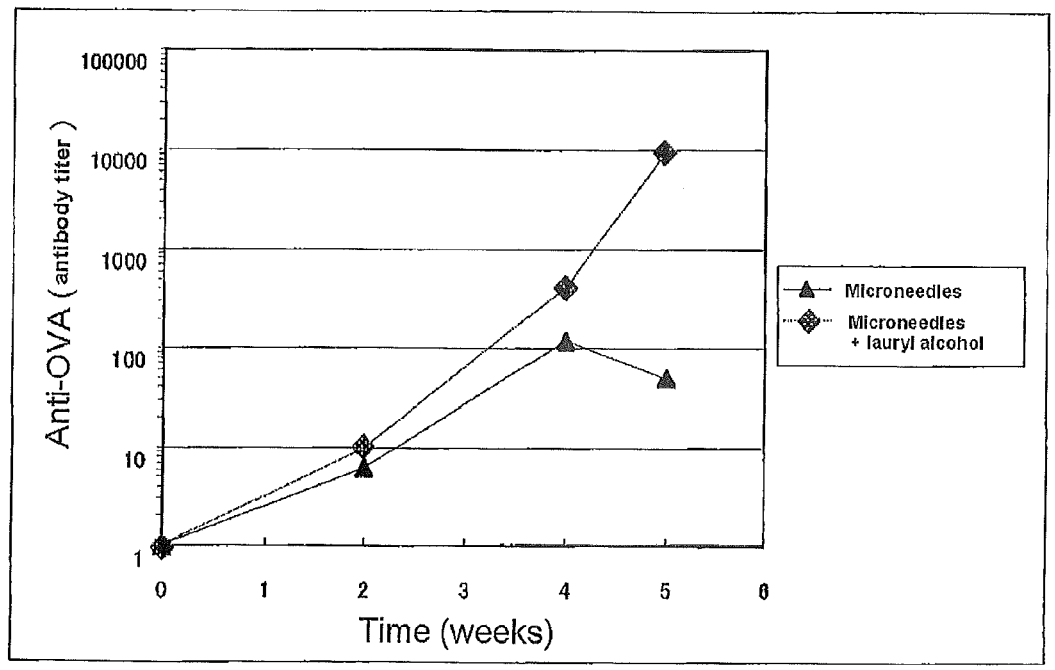
[FIG. 3] A diagram showing the effect of the adjuvant of the present invention by the combined use of LA in antigen-coated microneedles.
Figure 4:
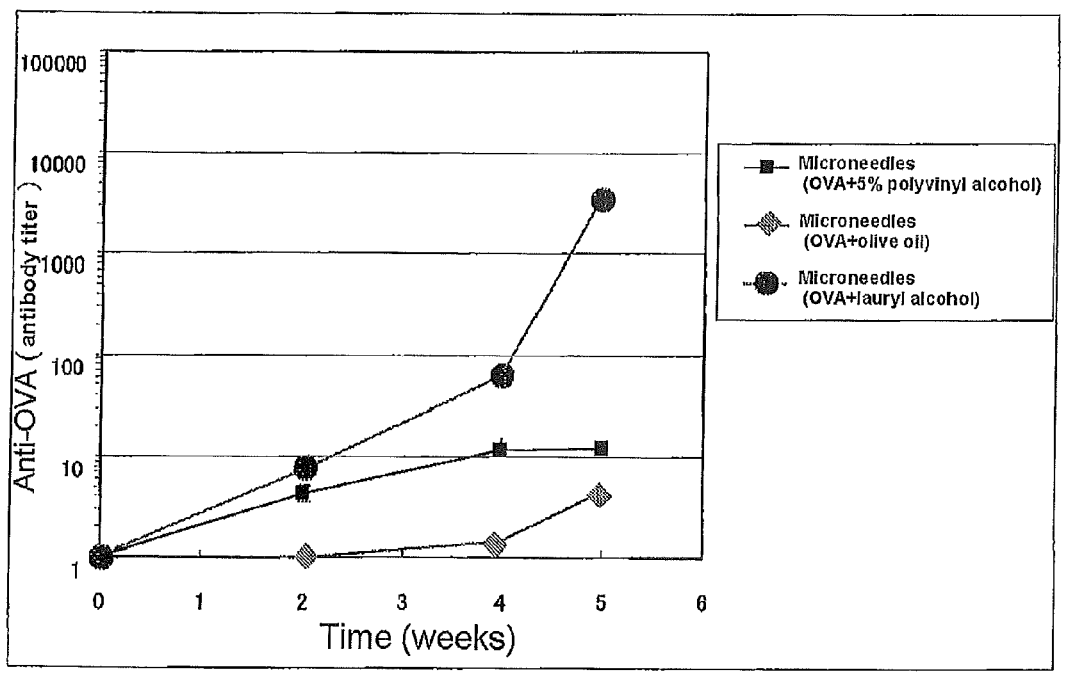
[FIG. 4] A diagram showing the effect of the adjuvant of the present invention, by coating microneedles with an emulsion of antigen+lauryl alcohol.
Figure 5:
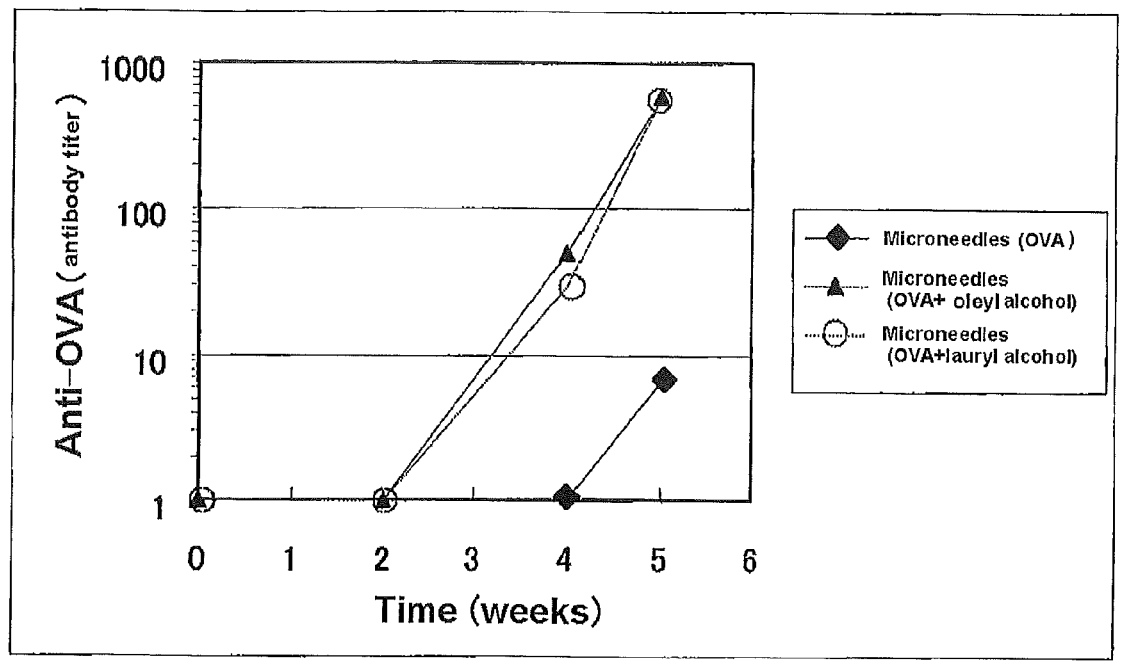
[FIG. 5] A diagram showing the effect of the adjuvant of the present invention by coating microneedles with an emulsion of antigen+lauryl alcohol or oleyl alcohol.
Figure 6:
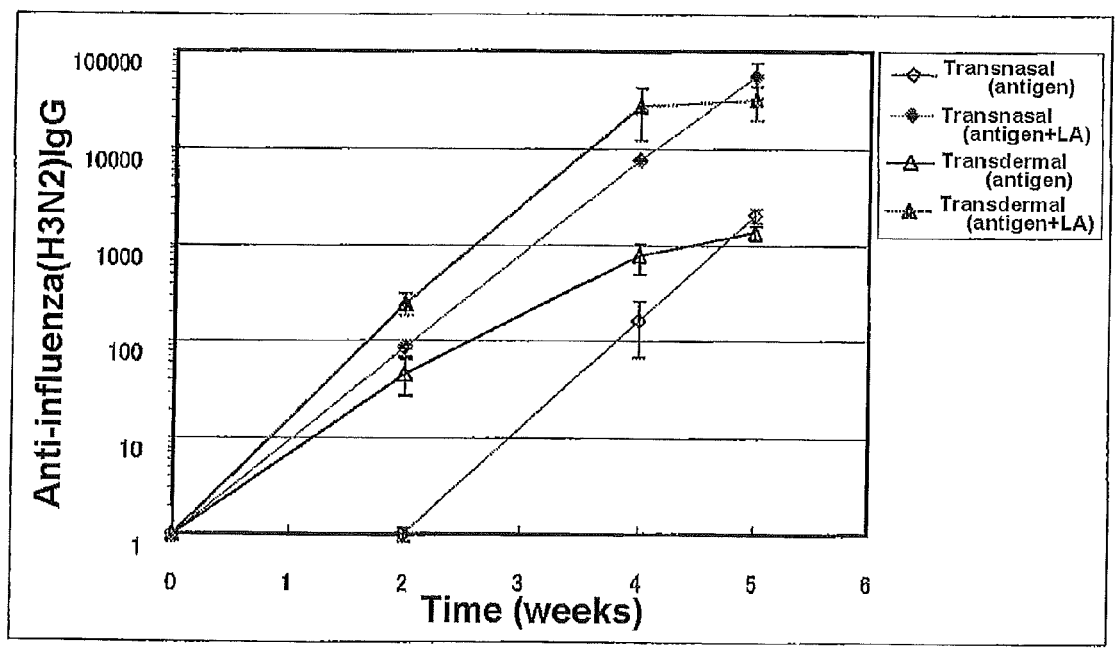
[FIG. 6] A diagram showing the effect of the adjuvant of the present invention by transnasal administration.
Figure 7:
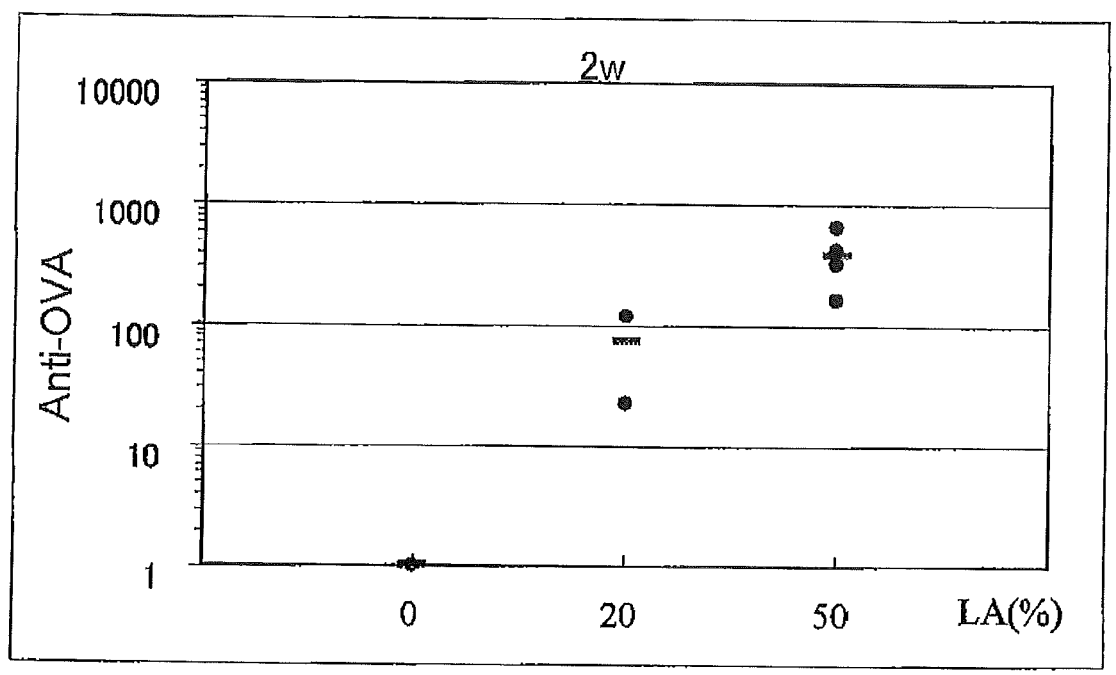
[FIG. 7] A diagram showing the effect of the adjuvant of the present invention by oral mucous membrane administration.

The invention claimed is:

1. A method for enhancing immunogenicity of a vaccine, said method comprising transdermally applying to skin an immunostimulatory adjuvant comprising at least one free fatty acid, and optionally at least one aliphatic alcohol, and
administering the vaccine by oral, injection, transmucosal or transdermal administration,
wherein at least one of the aliphatic alcohols is a saturated or unsaturated straight-chain or branched alcohol having 12 to 20 carbons, and wherein at least one of the free fatty acid is oleic acid so that immunogenicity of the vaccine is enhanced.

2. The method according to claim 1, wherein at least one of the aliphatic alcohols is lauryl alcohol, oleyl alcohol, isostearyl alcohol, or octyldodecanol.

3. A method for enhancing immunogenicity of a vaccine, said method comprising
transdermally applying to skin a pharmaceutical preparation comprising an immunostimulatory adjuvant comprising at least one free fatty acid, and optionally at least one aliphatic alcohol, and
administering the vaccine by oral, injection, transmucosal or transdermal administration,
wherein at least one of the aliphatic alcohols is a saturated or unsaturated straight-chain or branched alcohol having 12 to 20 carbons, and wherein at least one of the free fatty acid is oleic acid so that immunogenicity of the vaccine is enhanced.

4. The method according to claim 3, wherein the pharmaceutical preparation further comprises at least one vaccine.

5. The method according to claim 3, wherein the pharmaceutical preparation is at least one type of an ointment, a cream, a powder, a gel, a suppository, a poultice, a patch preparation, a lotion, a liquid, and a liniment.

6. The method according to claim 5, wherein the pharmaceutical preparation is a matrix type or layer type tape preparation or a reservoir type patch preparation.

7. The method according to claim 3, wherein the pharmaceutical preparation is applied to intact skin or mucous membrane or physically or chemically treated skin or mucous membrane.

8. The method to claim 7, wherein the physical or chemical treatment involves at least one of laser irradiation, skin abrasion, and microneedle, thermal, ultrasonic, electric field, magnetic field, pressure, and alkali treatments.

9. The method according to claim 3, wherein the pharmaceutical preparation is applied by at least one of skin abrasion, microneedle, and needle-free injection.

10. The method according to claim 9, wherein part or the whole surface of a needle portion of a microneedle is coated with a vaccine and/or an adjuvant.

11. The method according to claim 3, wherein the pharmaceutical preparation is applied by at least one of hydration, denaturing, pore formation, exfoliation, bypass formation, and change in lamellar structure of the stratum corneum.

12. The method according to claim 11, wherein the pharmaceutical preparation is applied by at least one of iontophoresis, sonophoresis, or electroporation.

13. The method according to claim 4, wherein the vaccine is selected from the group consisting of DNA vaccines, RNA vaccines and protein-based vaccines.

14. The method according to claim 3, wherein the pharmaceutical preparation contains 20 to 99 wt % of the immunostimulatory adjuvant.

15. The method according to claim 3, wherein at least one of the aliphatic alcohols is lauryl alcohol, oleyl alcohol, isostearyl alcohol, or octyldodecanol.

16. The method according to claim 1, wherein the immunostimulatory adjuvant comprises lauryl alcohol.

17. The method according to claim 3, wherein the immunostimulatory adjuvant comprises lauryl alcohol.

18. The method according to claim 1, wherein the vaccine is selected from the group consisting of DNA vaccines, RNA vaccines, and protein-based vaccines.

19. The method according to claim 1, wherein the vaccine is selected from the group consisting of proteins, polysaccharides, oligosaccharides, lipoproteins, attenuated or killed viruses and attenuated or killed bacteria, and mixtures thereof.

20. The method according to claim 3, wherein the vaccine is selected from the group consisting of proteins, polysaccharides, oligosaccharides, lipoproteins, attenuated or killed viruses and attenuated or killed bacteria, and mixtures thereof.

* * * * *